US012064368B2

(12) United States Patent
Gildersleeve et al.

(10) Patent No.: US 12,064,368 B2
(45) Date of Patent: Aug. 20, 2024

(54) ORTHOPEDIC SHOULDER-IMMOBILIZING APPARATUS

(71) Applicant: DJO, LLC, Vista, CA (US)

(72) Inventors: Richard E Gildersleeve, Carlsbad, CA (US); Tara VandenBerg, Rancho Santa Fe, CA (US); Thomas Bradley Edwards, Houston, TX (US); Sumant G. Krishnan, Dallas, TX (US); Lan Franklin, Vista, CA (US); David Orr, Vista, CA (US)

(73) Assignee: DJO, LLC, Carlsbad, CA (US)

( * ) Notice: Subject to any disclaimer, the term of this patent is extended or adjusted under 35 U.S.C. 154(b) by 47 days.

(21) Appl. No.: 17/160,784

(22) Filed: Jan. 28, 2021

(65) Prior Publication Data
US 2021/0228397 A1      Jul. 29, 2021

Related U.S. Application Data

(60) Provisional application No. 62/967,477, filed on Jan. 29, 2020.

(51) Int. Cl.
*A61F 5/37* (2006.01)

(52) U.S. Cl.
CPC .......... *A61F 5/3738* (2013.01); *A61F 5/373* (2013.01); *A61F 5/3753* (2013.01)

(58) Field of Classification Search
CPC ...... A61F 5/3738; A61F 5/373; A61F 5/3753; A61F 5/37; A61F 5/00; A61F 5/026;
(Continued)

(56) References Cited

U.S. PATENT DOCUMENTS

| | | | | | |
|---|---|---|---|---|---|
| 4,564,008 | A | * | 1/1986 | Donahoo | A61F 5/3738 602/4 |
| 6,610,022 | B1 | * | 8/2003 | Ashbaugh | A61F 5/028 602/19 |

(Continued)

FOREIGN PATENT DOCUMENTS

| JP | S62261362 A | 11/1987 |
|---|---|---|
| JP | 3197071 U | 4/2015 |

(Continued)

*Primary Examiner* — Alireza Nia
*Assistant Examiner* — Daniel A Miller
(74) *Attorney, Agent, or Firm* — Veros Legal Solutions, LLP

(57) ABSTRACT

A shoulder-immobilizing apparatus includes a forearm sling. The forearm sling is configured to receive an elbow, forearm and wrist of a first arm of a user and includes a first fastener configured for fastening a posterior strap to a proximal portion adjacent to the elbow, a second fastener configured for fastening an anterior strap to a distal portion adjacent to the wrist, and a contralateral strap holder. The contralateral strap holder includes a circumferential shoulder strap configured to wrap around a shoulder of a second arm of the user to form a substantially ellipsoid opening that seats against a pectoral region, a scapular region and one of an underarm region or a lateral outside portion of the shoulder of the user's second arm. The posterior and anterior straps each have swivel fasteners rotatably coupled to respective posterior and anterior portions of the circumferential shoulder strap. Related methods are also provided.

15 Claims, 11 Drawing Sheets

(58) Field of Classification Search
CPC .. A61F 5/05808; A61F 5/3723; A61F 5/3746; A61F 5/0111; A61F 5/028; A61F 5/05883; A61F 5/3715; A61F 5/01; A61F 5/0118; A61F 5/013; A61F 5/04; A61F 5/05; A61F 5/05841; A61F 5/05858; A61F 13/041; A61F 2/78; A61F 2002/742; A61F 2/74; A61F 2/742; A61F 5/30; A61F 5/32; A61F 5/34; A45F 3/04; A45F 3/14; A45F 3/02; A45F 3/06; A45F 2003/142; A45F 2003/146; A61B 17/135; A61B 17/1322; A61B 17/132; A45C 2013/028
USPC .............................................................. 602/4
See application file for complete search history.

(56) References Cited

U.S. PATENT DOCUMENTS

| | | |
|---|---|---|
| 7,189,213 B1 | 3/2007 | Weber |
| 7,244,239 B2 | 7/2007 | Howard |
| 7,300,410 B1 | 11/2007 | Weber |
| 8,414,512 B2 | 4/2013 | Fout |
| 8,523,795 B2 | 9/2013 | McCune et al. |
| 8,597,216 B2 | 12/2013 | Choudhury et al. |
| 8,992,451 B2 | 3/2015 | Fout |
| 9,498,369 B2 | 11/2016 | Kilbey |
| 9,895,254 B2 | 2/2018 | Bieber |
| 10,512,561 B2 | 12/2019 | Quigley et al. |
| 2004/0215119 A1* | 10/2004 | Avon .................. A61F 5/3738 602/4 |
| 2006/0258966 A1 | 11/2006 | Hargrave et al. |
| 2008/0119770 A1* | 5/2008 | Miller ................ A61F 5/3738 602/4 |
| 2012/0209159 A1* | 8/2012 | Fout .................... A61F 5/3738 602/4 |
| 2013/0317401 A1 | 11/2013 | Joslin |
| 2014/0228732 A1 | 8/2014 | Steinbaugh et al. |
| 2015/0047653 A1* | 2/2015 | Lo ....................... A61F 5/3753 128/878 |
| 2015/0250638 A1* | 9/2015 | Howard .............. A61F 5/3738 602/4 |
| 2015/0282630 A1* | 10/2015 | McIntyre ........... A47C 20/048 5/660 |
| 2016/0199212 A1 | 7/2016 | Turconi et al. |
| 2017/0156914 A1 | 6/2017 | Abel |
| 2018/0104086 A1 | 4/2018 | Cooper et al. |
| 2018/0133047 A1 | 5/2018 | Nakamitsu |
| 2019/0029866 A1* | 1/2019 | Stier ..................... A61F 5/026 |
| 2020/0306072 A1* | 10/2020 | Carney ................ A61F 5/0102 |

FOREIGN PATENT DOCUMENTS

| | | |
|---|---|---|
| JP | 2017047149 A | 3/2017 |
| JP | 2019030701 A | 2/2019 |
| WO | 2018201255 A1 | 11/2018 |

* cited by examiner

ORTHOPEDIC SHOULDER-IMMOBILIZING APPARATUS

CROSS-REFERENCE TO RELATED APPLICATIONS

This application claims priority to U.S. Provisional Application No. 62/967,477, filed on Jan. 29, 2020, the entire contents of which are hereby incorporated by reference.

TECHNICAL FIELD

The present disclosure relates generally to orthoses, and more particularly, to a shoulder sling for supporting and stabilizing a shoulder following surgery or injury.

BACKGROUND

The shoulder is a relatively complex joint of the body which is capable of rotation within multiple planes when the arm is displaced relative to the torso. Treatment of shoulder injury frequently requires determining a desired optimal treatment position of the shoulder and associated arm, and placement of the shoulder and arm in the desired treatment position. Such a recuperative treatment is particularly applicable to soft tissue injuries involving damage to one or more connective shoulder ligaments and, furthermore, is often the treatment of choice following any number of surgical procedures, such as, but not limited to, surgery for recurrent posterior subluxation, rotator cuff surgery, humeral head or shaft fracture correction, and similar.

Support devices for the shoulder, such as orthopedic braces, rigid casts, and slings are commonly used to perform such placement and immobilization. However, due at least in part to the use of one or more conventional shoulder straps that exert a substantial force on the neck of the user and, when multiple such straps are utilized can often be confusing for a user to put on, there remains a need for shoulder orthoses which provide greater comfort and versatility during immobilization, greater ease of use and less confusion for clinicians and/or patients.

SUMMARY

According to some embodiments, a shoulder-immobilizing apparatus is provided. The apparatus includes a forearm sling configured to receive an elbow, a forearm and a wrist of a first arm of a user. The forearm sling further includes a first fastener configured for fastening a posterior strap to a proximal portion of the forearm sling adjacent to the elbow of the user. The forearm sling further includes a second fastener configured for fastening an anterior strap to a distal portion of the forearm sling adjacent to the wrist of the user. The apparatus includes a contralateral strap holder. The contralateral strap holder includes a circumferential shoulder strap configured to wrap around a shoulder of a second arm of the user to form a substantially ellipsoid opening that seats against a pectoral region, a scapular region and one of an underarm region or a lateral outside portion of the shoulder of the second arm. The posterior strap has a first swivel fastener configured to rotatably couple to one or more positions on a posterior portion of the circumferential shoulder strap. The anterior strap has a second swivel fastener configured to rotatably couple to one or more positions on an anterior portion of the circumferential shoulder strap. The contralateral strap holder does not exert a force against a neck of the user.

According to some embodiments, a method of using a shoulder-immobilizing apparatus is provided. The method includes disposing an elbow, a forearm and a wrist of a first arm of a user into a forearm sling. The forearm sling includes a posterior strap fastened to a proximal portion of the forearm sling adjacent to the elbow of the user utilizing a first fastener and an anterior strap fastened to a distal portion of the forearm sling adjacent to the wrist of the user utilizing a second fastener. The method includes wrapping a circumferential shoulder strap of a contralateral strap holder of the shoulder-immobilizing apparatus around a shoulder of a second arm of the user to form a substantially ellipsoid opening that seats against a pectoral region, a scapular region and one of an underarm region and a lateral outer portion of the shoulder of the second arm. The method includes rotatably coupling a first swivel fastener of the posterior strap to one or more positions on a posterior portion of the circumferential shoulder strap. The method includes rotatably coupling a second swivel fastener of the anterior strap to one or more positions on an anterior portion of the circumferential shoulder strap, wherein the contralateral strap holder does not exert a force against a neck of the user.

BRIEF DESCRIPTION OF THE DRAWINGS

While the appended claims set forth the features of the present techniques with particularity, these techniques, together with their objects and advantages, may be best understood from the following detailed description taken in conjunction with the accompanying drawings of which:

DETAILED DESCRIPTION OF EXEMPLARY EMBODIMENTS

Figure 1:
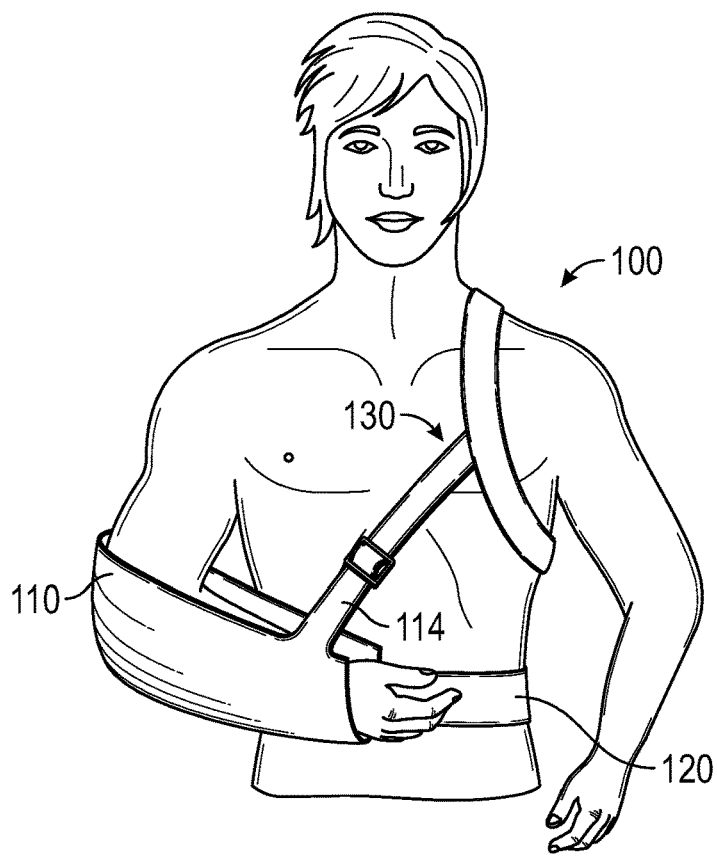
FIG. 1 illustrates a shoulder immobilizing apparatus disposed on a user, in accordance with some example embodiments.

Turning to the drawings, wherein like reference numerals refer to like elements, techniques of the present disclosure are illustrated as being implemented in a suitable environment. The following description is based on embodiments of the claims and should not be taken as limiting the claims with regard to alternative embodiments that are not explicitly described herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The word "orthosis" or "orthotic" is used herein to mean a brace, sling or other such device. Consequently, orthosis may be used interchangeably with the term "brace" and/or "sling" and may refer to specific types of braces and/or slings when indicated (e.g., a shoulder orthosis, shoulder brace, and/or shoulder sling).

A better understanding of the various features of the disclosure can be gleaned from the following description read in conjunction with the accompanying drawings in which like reference characters refer to like elements, where reasonably applicable. While the disclosure may be susceptible to various modifications and alternative constructions, certain illustrative features are shown in the drawings and are described in detail below. It will be understood, however, that there is no intention to limit the disclosure to the specific embodiments disclosed, but to the contrary, the intention is to cover all modifications, alternative constructions, combinations, and equivalents falling within the spirit and scope of the disclosure.

Furthermore, it will be appreciated that unless a term is expressly defined in this disclosure to possess a described meaning, there is no intent to limit the meaning of such term, either expressly or indirectly, beyond its plain or ordinary meaning.

For ease of understanding the disclosed features of an orthopedic device, as used herein, "proximal" has its ordinary meaning and refers to a location situated next to or near the point of attachment or origin or a central point or located toward the center of the body. Likewise, the term "distal" has its ordinary meaning and refers to a location that is situated away from the point of attachment or origin or central point or located away from the center of the body. The term "medial" refers to a position that is closer to the midline of the body, whereas the term "lateral" refers to a position further from the midline of the body. The term "posterior" also has its ordinary meaning and refers to a location that is behind or to the rear of another location or feature. Lastly, the term "anterior" has its ordinary meaning and refers to a location that is ahead of or to the front of another location or feature.

The terms "rigid," "flexible," "malleable" and "resilient" may be used herein to distinguish portions of certain features of the orthopedic device. The term "rigid" is intended to mean an element of the device is generally or substantially inflexible. Within the context of frame or support members or shells that are "rigid," it is intended to indicate that they do not lose their overall shape when force is applied. The term "flexible" or "malleable", by contrast, is intended to encompass features that are capable of bending or flexing under load.

Embodiments of this disclosure relate to a shoulder sling for immobilization of the shoulder. Advantages of a shoulder sling according to one or more embodiment described herein include lightweight construction, easy application, quick and easy customization and/or adjustment of one or more dimensions of the sling for a more precise and/or comfortable fit for the user, quick and easy adjustable abduction and/or external/internal rotation, and ease of convertibility from left to right shoulder user or vice versa. Additional features include the ability to employ a precise amount of abduction and external/internal rotation as well as a breathable design.

Current products on the market are bulky and employ one or more shoulder straps which can impinge on the nerves in the area of the clavicle (e.g., proximal and/or medial portion of the clavicle) causing neck pain and discomfort. By using, among other potential features, a contralateral strap holder configured to support the sling and/or rest against pectoral, scapular and underarm regions of the contralateral side of the user's body compared to the shoulder/arm being immobilized by the sling, shoulder devices or orthosis provided herein eliminate the need for conventional neck straps, thus eliminating the associated pain and discomfort. Additionally, the low-profile design of the device reduces the bulk and weight seen in other designs and allow for more breathability and/or adjustability thus reducing patient discomfort while wearing the orthosis. The sling described herein immobilizes and supports a wearer's arm and shoulder with comfort, compliance, and convenience as compared with prior sling designs. Indeed, the sling disclosed herein affords a multitude of advantages for someone who is recovering from shoulder injury, rotator cuff surgery, or otherwise has a soft tissue strain. As will be described in greater detail below, the telescoping, adjustable strap system and universal sized sling can accommodate a wide range of patient sizes. Moreover, the sling can fit the right or left arm of the wearer.

In some embodiments, multiple pathologies can be addresses with one orthosis, including, but not limited to: glenohumeral dislocation or subluxation, capsular shifts, posterior shoulder stabilizations, Bankart repairs, release severe anterior capsule contracture, soft tissue strains or repairs, rotator cuff repairs, total shoulder replacement, superior labral repairs (SLAP), shoulder debridement, fractures (humerus, elbow, forearm), biceps tendon repair, elbow ligament/tendon repair, anterior shoulder luxation and AC joint reconstruction.

Discussion of one or more embodiments of a shoulder immobilizing apparatus according to this disclosure will now be discussed below in connection with one or more figures.

Figure 2A:
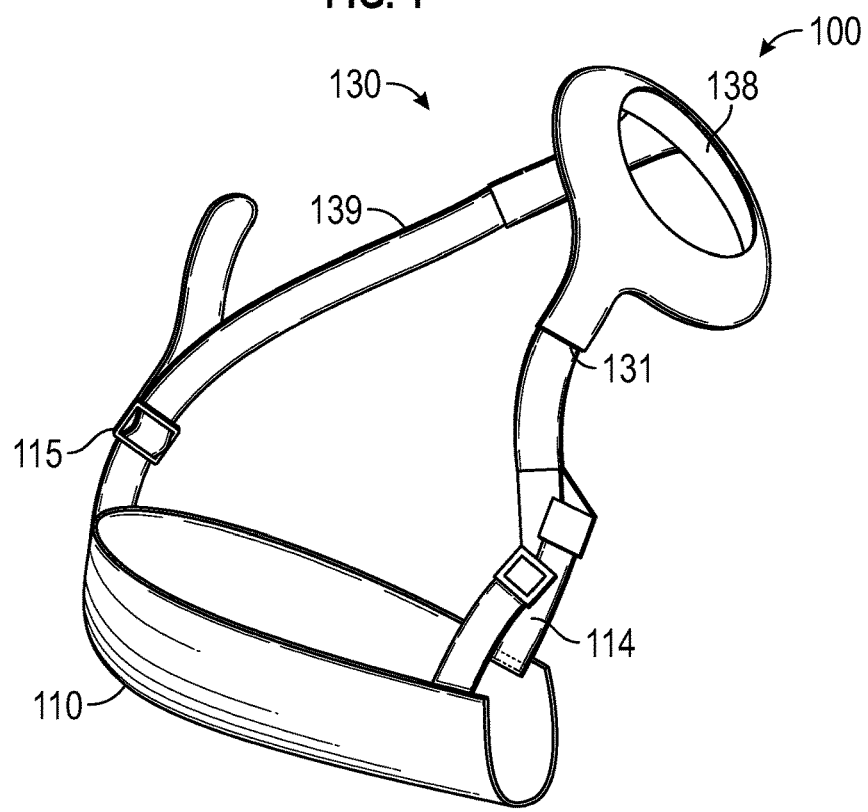
FIG. 2A illustrates the shoulder immobilizing apparatus of FIG. 1 without the user illustrated for easy reference, in accordance with some example embodiments.
Figure 2B:
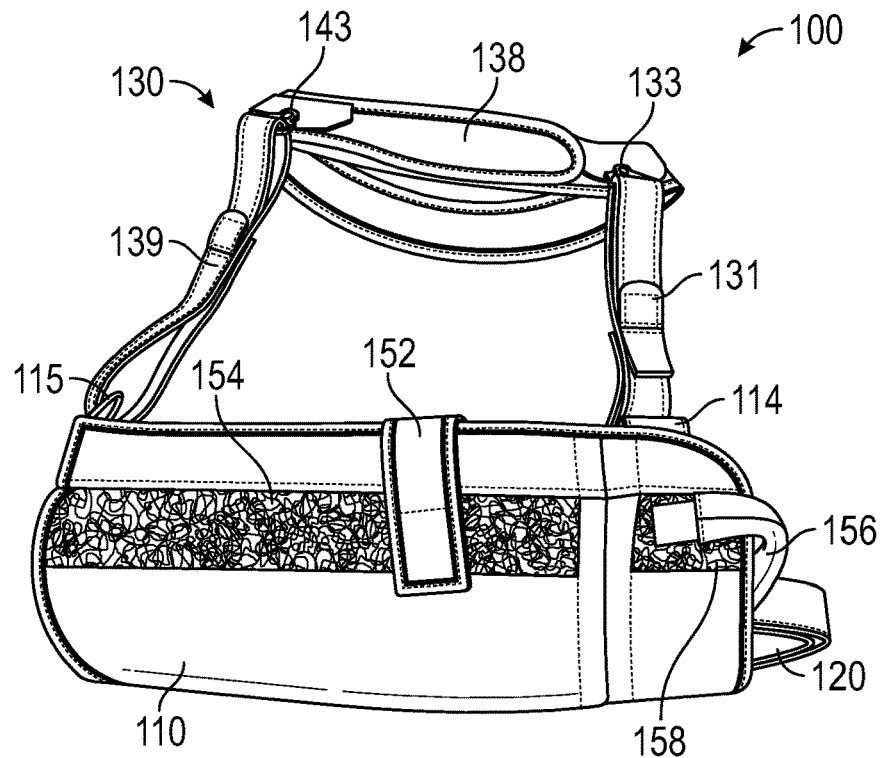
FIG. 2B also illustrates the shoulder immobilizing apparatus of FIG. 1, in accordance with some example embodiments.

FIG. 1 illustrates a shoulder immobilizing apparatus 100 disposed on a user, in accordance with some example embodiments. FIGS. 2A and 2B illustrate the shoulder immobilizing apparatus 100 of FIG. 1 without the user illustrated for easy reference, in accordance with some example embodiments. Shoulder-immobilizing apparatus 100 comprises a forearm sling 110 configured to receive an elbow, a forearm and a wrist of a first arm of a user. Forearm sling 110 and associated examples thereof will be discussed in more detail in connection with at least FIGS. 3-7 below.

Forearm sling 110 further comprises a first fastener 115 configured for fastening a posterior strap 139 to a proximal portion of the forearm sling 110 adjacent to the elbow of the user when the arm of the user is properly disposed in the sling 110. In some embodiments, first fastener 115 can comprise one or more of a buckle, a ring, a strap receiving-slot, hook and loop fasteners, or any other suitable means for fastening a strap to the proximal portion of the forearm sling 110.

Forearm sling 110 further comprises a second fastener 114 configured for fastening an anterior strap 131 to a distal portion of forearm sling 110 adjacent to the wrist of the user when the arm of the user is properly disposed in sling 110. In some embodiments, second fastener 114 can comprise one or more of a buckle, a ring, a strap receiving-slot, hook and loop fasteners, or any other means for fastening a strap to the distal portion of forearm sling 110. In some embodiments, second fastener 114 can comprise two such buckles, rings, strap receiving-slots or other means for fastening a strap to the distal portion of forearm sling 110. In some such embodiments, each such buckle, ring, strap receiving-slot or other fastening means may be configured to fasten anterior strap 131 to distal portions of forearm sling 110, on either upper edge of forearm sling 110, adjacent to the wrist of the user. In some such embodiments, at least one such buckle, ring, strap receiving slot or other fastening means may also be configured to attach and/or couple forearm sling 110 to a waist strap 120.

In some embodiments, forearm sling 110 further comprises a third fastener 152 configured for fastening around a wrist of the user when the arm of the user is properly disposed in sling 110. In some embodiments, third fastener 152 can comprise hook and loop fasteners (or any other suitable fastening means) configured to releasably couple to at least a compatible portion 154 of forearm sling 110 disposed substantially between the distal portion of forearm sling 110 where anterior strap 131 is fastened to forearm sling 110 and the proximal portion of the forearm sling 110 where posterior strap 139 is fastened to forearm sling 110.

In some embodiments, forearm sling 110 further comprises a fourth fastener 156 configured for fastening around at least a portion of a hand of the user when the arm of the user is properly disposed in sling 110. For example, fourth fastener 156 can be configured to extend between a thumb and a forefinger of the hand of the arm disposed in sling 110 such that the hand and/or arm of the user is further secured to and/or restrained within sling 110. In some embodiments, fourth fastener 156 can comprise hook and loop fasteners (or any other suitable fastening means) configured to releasably couple to at least a compatible portion 158 of forearm sling 110 disposed at a distal portion of forearm sling 110.

Figure 8:
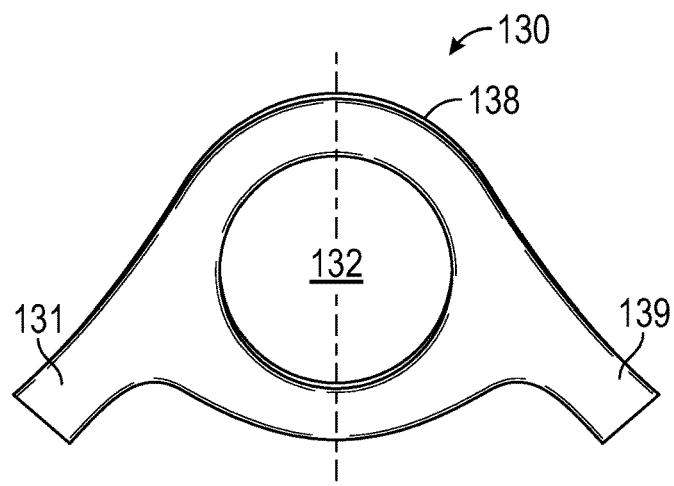
FIG. 8 illustrates a circumferential shoulder strap of a shoulder immobilizing apparatus, in accordance with some example embodiments.

Forearm sling 110 further comprises a contralateral strap holder 130. Strap holder 130 comprises a circumferential shoulder strap 138 configured to wrap around a shoulder of a second arm of the user to form a substantially ellipsoid opening 132 (see, e.g., FIG. 8) that seats against at least a pectoral region, a scapular region and one of an underarm region (see, e.g., FIGS. 1, 11A and 11B) or lateral outer portion (see, e.g., FIG. 10) of the contralateral shoulder of the second arm of the user. Contralateral strap holder 130, circumferential shoulder strap 138 and associated examples and/or portions thereof will be discussed in more detail in connection with at least one of FIGS. 8-11B below.

The disclosure now turns to aspects of one or more example forearm slings 110, 310, 410, 510, 610, 710 as described in connection with at least FIGS. 1-7. In some embodiments, one or more of forearm slings 110, 310, 410, 510, 610, 710 comprises a light, breathable, non-slip material. In some embodiments, one or more of forearm slings 110, 310, 410, 510, 610, 710 comprises an inner mesh, a full liner, and/or an outer sleeve, which, in some cases can comprise a foam material and a plurality of breathable holes disposed therein.

Figure 3:
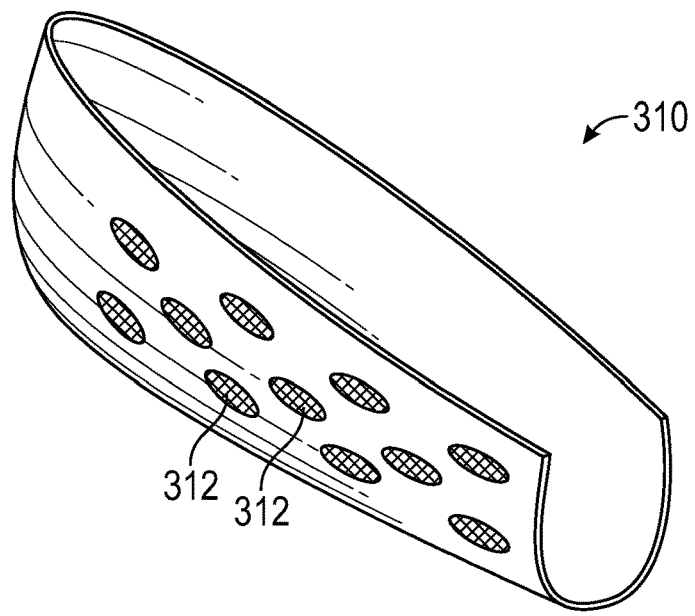
FIG. 3 illustrates a forearm sling of a shoulder immobilizing apparatus, having a plurality of breathable holes, in accordance with some example embodiments.

For example, FIG. 3 illustrates a forearm sling 310 of a shoulder immobilizing apparatus, having a plurality of breathable holes 312, in accordance with some example embodiments. In some such embodiments, breathable holes 312 can have substantially circular or slightly elongated shape(s). In some embodiments, breathable holes 312 may have a maximum diameter that prevents window edema (e.g., 1/16th of an inch or less). However, the present disclosure is not so limited and breathable holes 312 can have any shape and/or size suitable for the application(s) discussed here.

Figure 4:
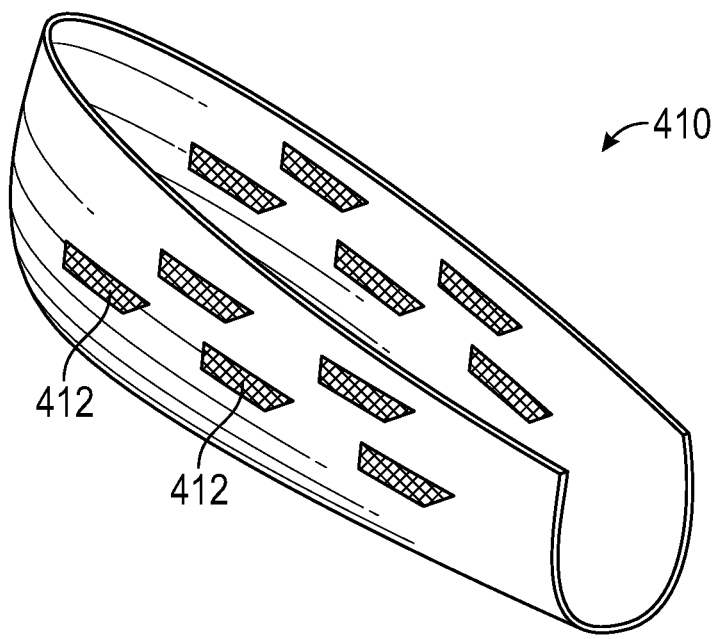
FIG. 4 illustrates another forearm sling of a shoulder immobilizing apparatus, having a plurality of elongated breathable holes, in accordance with some example embodiments.

As yet another example, FIG. 4 illustrates another forearm sling 410 of a shoulder immobilizing apparatus, having a plurality of elongated breathable holes 412, in accordance with some example embodiments. In some such embodiments, breathable holes 412 can have substantially elongated shape(s). e.g., ovoid, rectangular, and/or rectangular with substantially rounded corners. In some embodiments, breathable holes 412 may have a maximum diameter that prevents window edema (e.g., 1/16th of an inch or less). However, the present disclosure is not so limited and breathable holes 412 can have any shape and/or size suitable for the application(s) discussed here.

Figure 5:
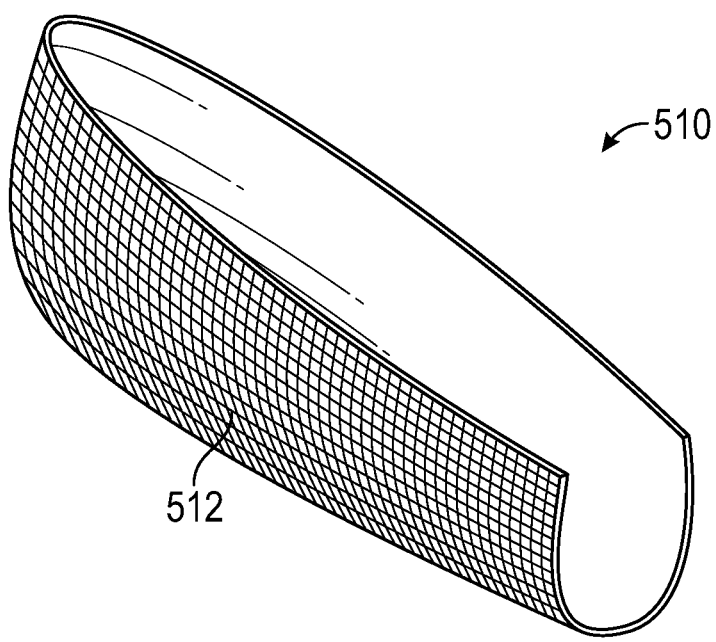
FIG. 5 illustrates yet another forearm sling of a shoulder immobilizing apparatus, having a substantially open mesh, in accordance with some example embodiments.

As yet another example, FIG. 5 illustrates yet another forearm sling 512 of a shoulder immobilizing apparatus, having a substantially open mesh 512, in accordance with some example embodiments. In some such embodiments, substantially open mesh 512 may be such that the openings portion of mesh 512 comprise a substantial majority of the surface area of forearm sling 510. In some embodiments, the openings in substantially open mesh 512 may have a maximum diameter that prevents window edema (e.g., 1/16th of an inch or less). However, the present disclosure is not so limited and the openings in substantially open mesh 512 can have any shape and/or size suitable for the application(s) discussed in this disclosure.

Figure 6:
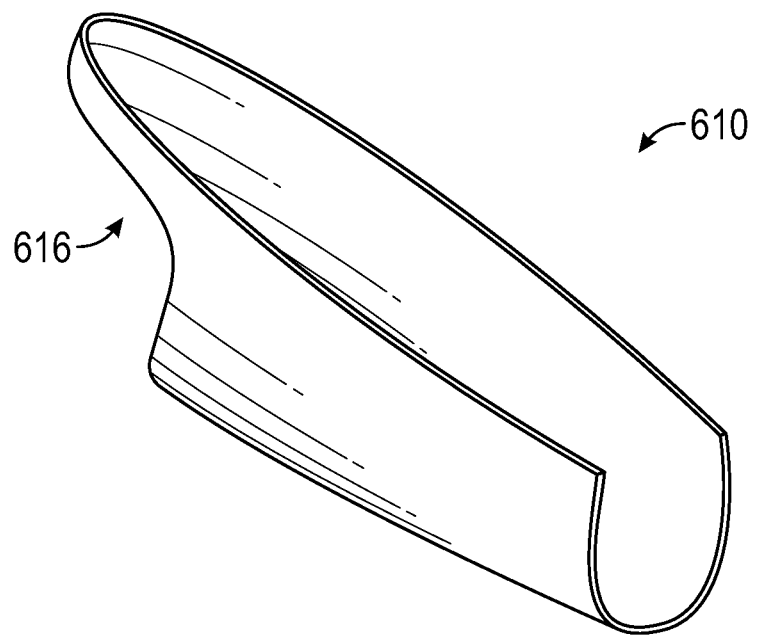
FIG. 6 illustrates yet another forearm sling of a shoulder immobilizing apparatus, having a cutout configured to expose an elbow of a user, in accordance with some example embodiments.

In some embodiments, one or more of forearm slings 110, 310, 410, 510, 610, 710 comprises one or more cutouts for increased comfort of the user. For example, FIG. 6 illustrates yet another forearm sling 610 of a shoulder immobilizing apparatus, having a cutout 616 configured to expose an elbow of a user when the user's arm is properly disposed in the forearm sling 610, in accordance with some example embodiments. In some such embodiments, forearm sling 610 does not contact at least a portion of the elbow of the first arm of the user when the first arm is properly disposed within the sling 100, reducing or eliminating associated pressure points and increasing user comfort.

Figure 7:
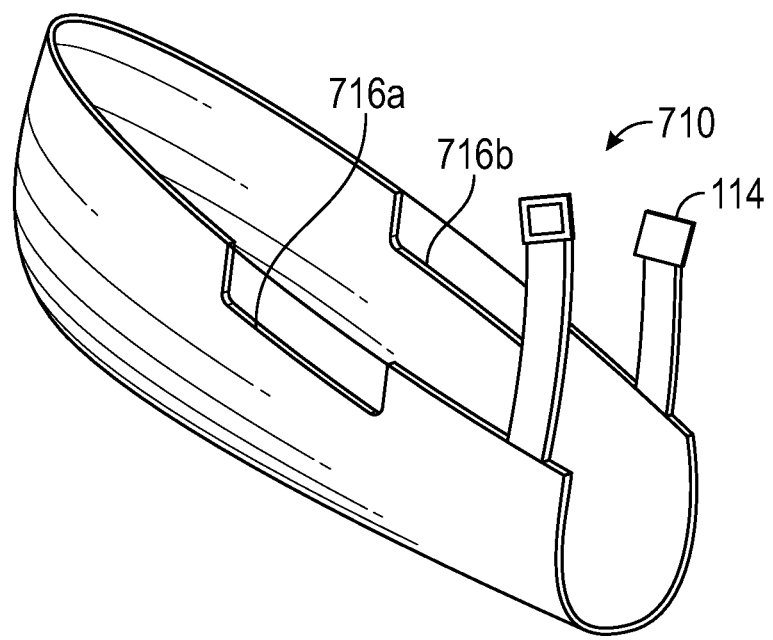
FIG. 7 illustrates yet another forearm sling that can comprise one or more cutout(s) configured to expose an upper portion of the forearm of a user, in accordance with some example embodiments.

In addition or alternative, as illustrated in FIG. 7, yet another forearm sling 710 can comprise one or more cutout(s) 716a, 716b configured to expose an upper portion of the forearm of a user, in accordance with some example embodiments. In some such embodiments, forearm sling 710 does not contact one or more portions of the user's forearm along a top edge of forearm sling 710 to further increase user comfort.

While several embodiments of a forearm sling are described in connection with FIGS. 1-7 above, the present disclosure also contemplates any and all embodiments comprising any combination of features described in connection with any of the forearm slings herein, in a single forearm sling, in some cases, even including embodiments where the forearm sling comprises a full sleeve that is not substantially open at its top, as is illustrated in any of FIGS. 1-7.

The disclosure now turns to discussion of aspects of one or more example contralateral strap holders 130 as described in connection with at least FIGS. 1-2B and 8-11B. As briefly described above in connection with FIGS. 1-2B, contralateral strap holder 130 comprises a circumferential shoulder strap 138 configured to wrap around a shoulder of a second arm of the user to form a substantially ellipsoid opening 132, or arm loop, that seats against at least a pectoral region, a scapular region and one of an underarm region or a lateral outside portion of the shoulder of the second, or contralateral, arm of the user. In some embodiments, substantially ellipsoid opening 132 can be substantially circular in cross-section. In some embodiments, substantially ellipsoid opening 132 can be substantially ovoid or elliptical in cross-section. In some embodiments, substantially ellipsoid opening 132 is substantially symmetrical about the dashed line illustrated in FIG. 8 such that sling 100 can be used on either shoulder without significant adjustment. In some embodiments, circumferential shoulder strap 138 can further comprise padding that further increases the comfort for the user.

As illustrated in at least one of FIGS. 1-2B, 8 and 9, anterior strap 131 can be coupled and/or couplable to an anterior portion of circumferential shoulder strap 138, while posterior strap 139 can be coupled and/or coupleable to one or more positions on a posterior portion of circumferential shoulder strap 138. As will be described in more detail in connection with FIGS. 11A and 11B, and as additionally illustrated in at least FIG. 2B, posterior strap 139 can have a first swivel fastener 143 configured to rotatably couple to one or more positions on a posterior portion of circumferential shoulder strap 138. Similarly, anterior strap 131 can have a second swivel fastener 133 configured to rotatably couple to one or more positions on an anterior portion of circumferential shoulder strap 138. In this way, one or both of anterior strap 131 and posterior strap 139 are configured to extend, unwrinkled and unfolded, between forearm sling 110 and circumferential shoulder strap 138.

Because the circumferential shoulder strap 138 is configured to wrap around the contralateral shoulder of the user to form a substantially ellipsoid opening that seats against a pectoral region, a scapular region and one of an underarm region or lateral outside portion of the shoulder of the second arm, contralateral strap holder 130 does not exert a force against a neck of the user as do conventional straps that wrap around the neck or substantially only along a top portion of the contralateral shoulder.

Figure 9:
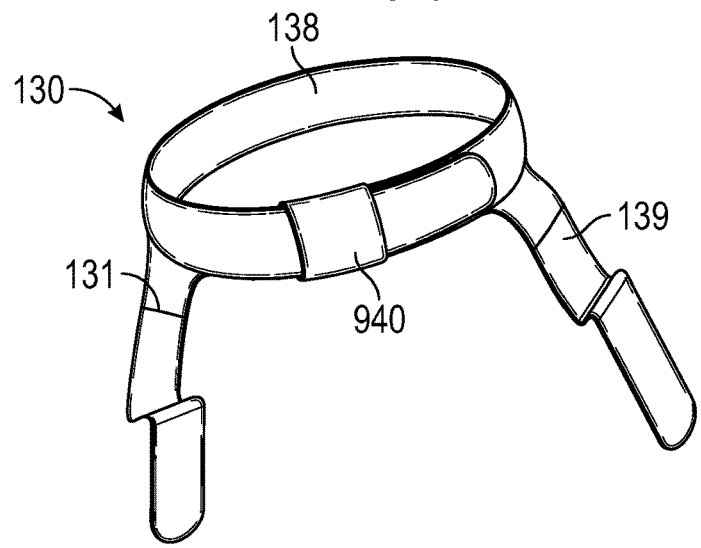
FIG. 9 illustrates an adjustable aspect of a circumferential shoulder strap of a shoulder immobilizing apparatus, in accordance with some example embodiments.

In some embodiments, for example as illustrated in connection with at least FIG. 9, the user can adjust a size of substantially ellipsoid opening 132 by adjusting an amount of overlap at opposite ends 940 of shoulder strap 138, which can be coupled to one another via any suitable type of fastener, e.g., hook and loop-type fasteners disposed on one or both ends 940 of shoulder strap 138. In some embodiments, opposite ends 940 of shoulder strap 138 overlap one another at a top of substantially ellipsoid opening 132, e.g., at a portion of substantially ellipsoid opening 132 configured to rest against a top of the contralateral shoulder of the second arm, rather than substantially only against a pectoral, scapular or underarm portion of the contralateral shoulder of the second arm. Opposite ends 940 of shoulder strap 138 overlapping one another at a top of substantially ellipsoid opening 132 has been found to be significantly more convenient for practitioners and medical staff to put forearm sling 100 on a patient while the patient is still unconscious or otherwise immobilized, compared to opposite ends 940 of shoulder strap 138 overlapping one another at another portion of ellipsoid opening 132 (e.g., at a bottom or underarm portion of substantially ellipsoid opening 132), which can interfere with heavy, larger arms of larger patients and/or wires transmitting vitals during and/or after surgery. The specific design of the forearm slings described by this disclosure are easier and less confusing for clinicians and patients to use, compared to conventional slings, since knowing substantially ellipsoid opening 132 is configured to encircle the contralateral shoulder of the second arm makes it simple to properly extend anterior strap 131 across the anterior of the patient's body, torso and/or chest and posterior strap 139 across the posterior of the patient's body, torso and/or chest.

Figure 10:
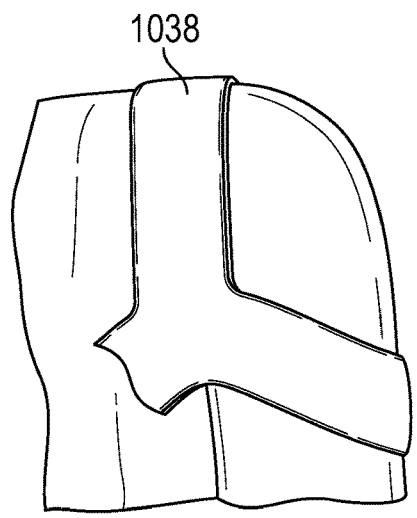
FIG. 10 illustrates an over-arm orientation of a circumferential shoulder strap of a shoulder immobilizing apparatus, in accordance with some example embodiments.

In some embodiments, for example as illustrated in connection with at least FIG. 10, an alternative circumferential shoulder strap 1038 can be configured in an over-arm orientation such that a portion corresponding to the portion of shoulder strap 138 shown in FIGS. 1 and 2 as extending around an underside of the user's contralateral arm (e.g., arm pit) instead extends around an outside, lateral portion of the user's contralateral arm. In such embodiments, shoulder strap 1038 may be configured to exert a force against the outside, lateral portion of the user's contralateral arm, rather than to the underside of the user's contralateral arm while still providing similar neck-pain reducing benefits as the under-arm embodiments, such as those described in connection with at least FIGS. 1-2B. In such embodiments, circumferential shoulder strap 1038 may have substantially the same features as shoulder strap 138 except that portion of strap 1038 corresponding to the portion of shoulder strap 138 configured to be disposed along the underarm of the contralateral shoulder is instead configured to be disposed along and/or around a lateral portion of the patient's contralateral shoulder for circumferential shoulder strap 1038.

Figure 11A:
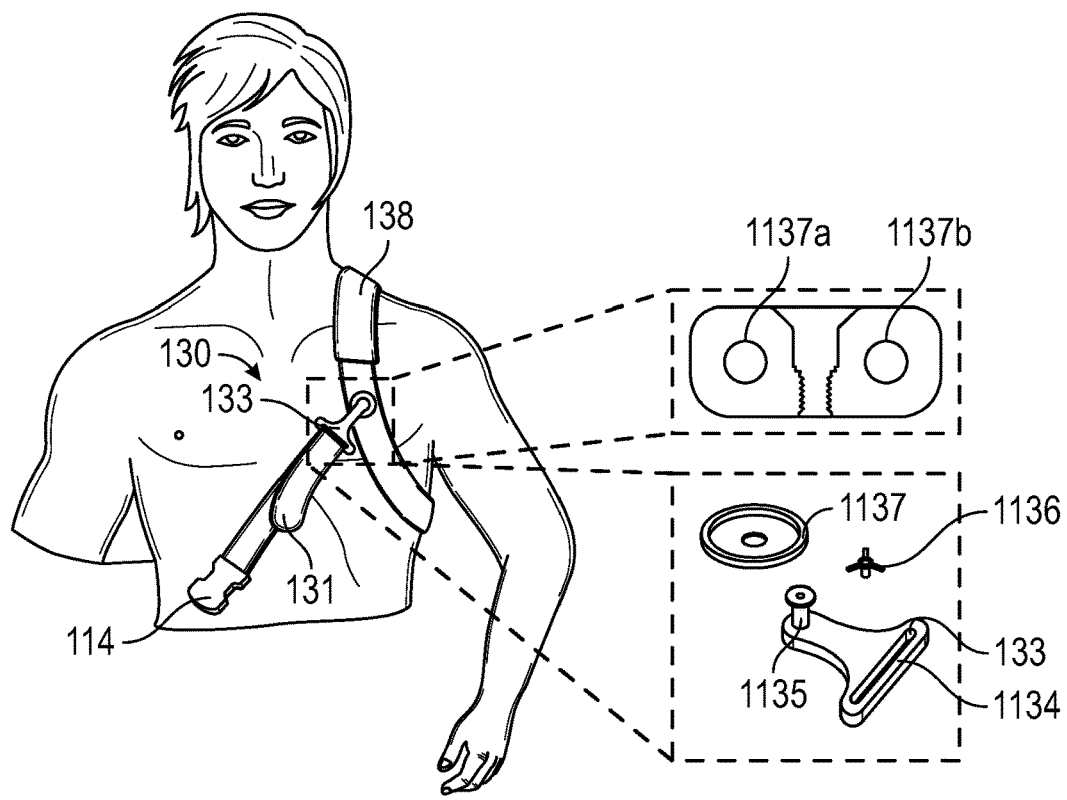
FIG. 11A illustrates a swivel fastener configured to rotatably couple an anterior strap to an anterior portion of a circumferential shoulder strap, in accordance with some example embodiments.

The disclosure now turns to discussion of aspects of one or more example rotatable couplings between one or both of anterior strap 131 and posterior strap 139 and respective portions of circumferential shoulder strap 138, 1038 as described in connection with at least FIGS. 1-2B, 11A and 11B. For example, FIG. 11A illustrates swivel fastener 133 configured to rotatably couple anterior strap 131 to an anterior portion of circumferential shoulder strap 138, 1038, thereby allowing anterior strap to extend, unwrinkled and unfolded, between forearm sling 110 and circumferential shoulder strap 138, 1038, in accordance with some example embodiments. Swivel fastener 133 can include one 1137 or more sew-down fabric grommet(s) 1137*a*, 1137*b* configured to be sewn into or otherwise secured at one or more locations on an anterior portion of circumferential shoulder strap 138, 1038, as well as a buckle having a slot 1134 configured to receive anterior strap 131 and a swivel post 1135 (e.g., a snap swivel post) having a locking feature 1136 (e.g., a D-ring snap lock) configured to secure swivel post 1135 to the one 1137 or to one of the more than one fabric grommet (s) 1137*a*, 1137*b*. In some embodiments, the fabric grommets 1137*a*, 1137*b* can also have different colored, numbered or otherwise denoted stickers, patches and/or identifiers to easily guide the user to the appropriate grommet for a proper, secure, comfortable fit of apparatus 100.

Figure 11B:
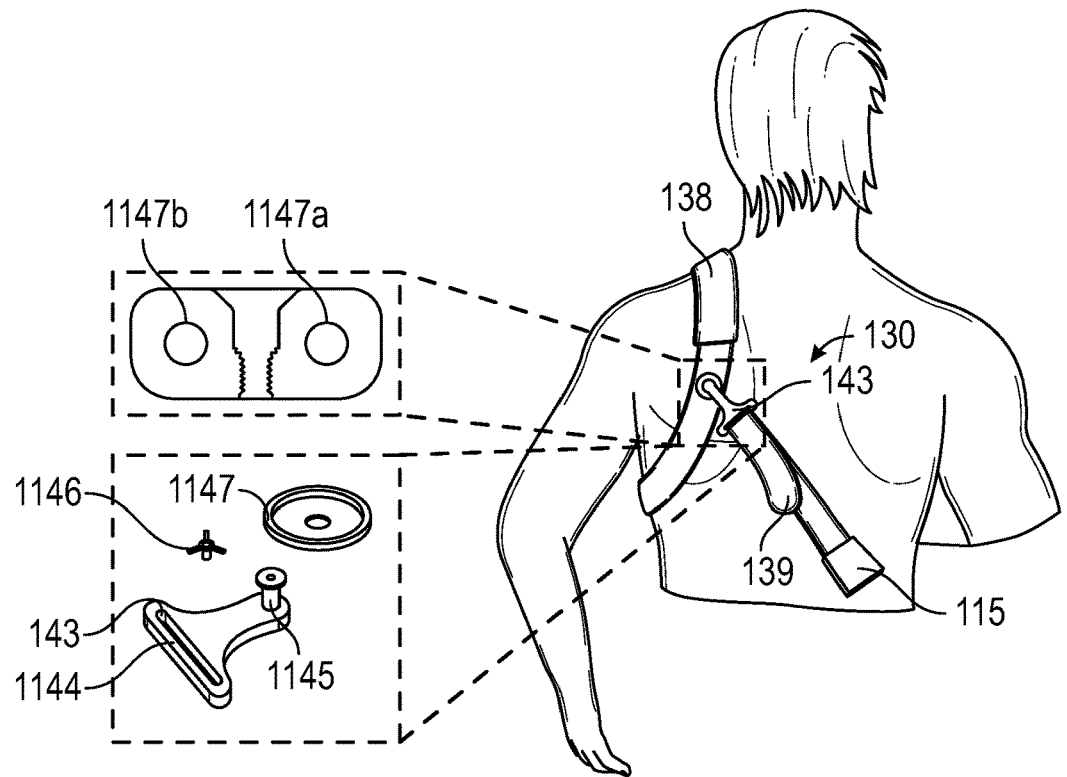
FIG. 11B illustrates a swivel fastener configured to rotatably couple a posterior strap to a posterior portion of a circumferential shoulder strap, in accordance with some example embodiments.

In some embodiments, a similar swivel fastener can be utilized for coupling posterior strap 139 to the posterior portion of circumferential shoulder strap 138, 1038 as described above for anterior strap 131, thereby allowing posterior strap 139 to extend, unwrinkled and unfolded, between forearm sling 110 and circumferential shoulder strap 138, 1038. For example. FIG. 11B illustrates swivel fastener 143 configured to rotatably couple posterior strap 139 to a posterior portion of circumferential shoulder strap 138, 1038, thereby allowing posterior strap to extend, unwrinkled and unfolded, between forearm sling 110 and circumferential shoulder strap 138, 1038, in accordance with some example embodiments. Swivel fastener 143 can include one 1147 or more sew-down fabric grommet(s) 1147*a*, 1147*b* configured to be sewn into or otherwise secured at one or more locations on a posterior portion of circumferential shoulder strap 138, 1038, as well as a buckle having a slot 1144 configured to receive posterior strap 139 and a swivel post 1145 (e.g., a snap swivel post) having a locking feature 1146 (e.g., a D-ring snap lock) configured to secure swivel post 1145 to the one 1147 or to one of the more than one fabric grommet(s) 1147*a*, 1147*b*. In some embodiments, the fabric grommets 1147*a*, 1147*b* can also have different colored, numbered or otherwise denoted stickers, patches and/or identifiers to easily guide the user to the appropriate grommet for a proper, secure, comfortable fit of apparatus 100.

Figure 12:
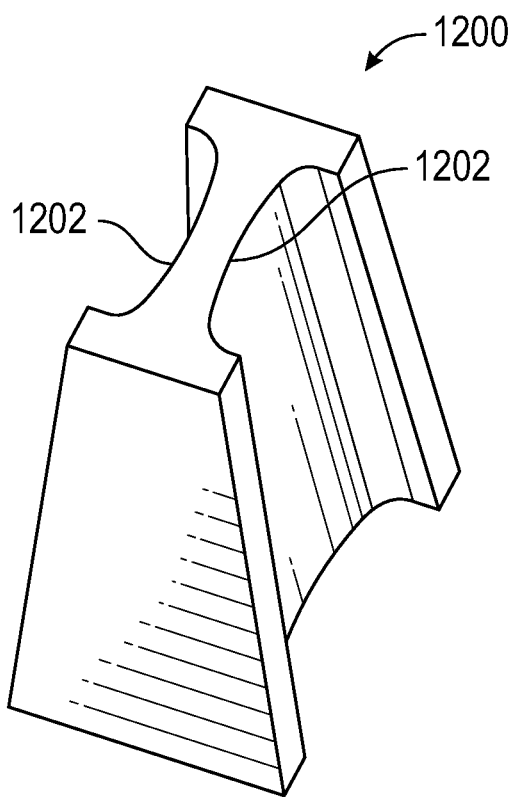
FIG. 12 illustrates an abduction cushion for a shoulder immobilizing apparatus, in accordance with some example embodiments.

The disclosure now turns to discussion of aspects of one or more example abduction cushions 1200, 1300, 1400, 1500, 1600, 1700 for achieving a desired abduction angle of the arm of the user with respect to his or her torso, as described in connection with at least FIGS. 12-17 below. For example. FIG. 12 illustrates an abduction cushion 1200 for a shoulder immobilizing apparatus, in accordance with some example embodiments. Abduction cushion 1200 is illustrated as having a unitary construction and having one end with a first thickness and an opposite end having a second thickness greater than the first thickness. Accordingly, abduction cushion 1200 may have a substantially wedge shape. Abduction cushion 1200 may comprise any suitable cushion material, for example and not limitation, memory foam, a mattress material, or another foam or padded material. In some embodiments, abduction cushion 1200 can further comprise one or more concave portions 1202 configured to secure abduction cushion 1200 between the user's immobilized arm and/or forearm and torso and establish the desired abduction angle. In some embodiments, one or more versions of abduction cushion 1200 having various thicknesses and wedge angles can be used to establish the desired abduction angle.

Figure 13:
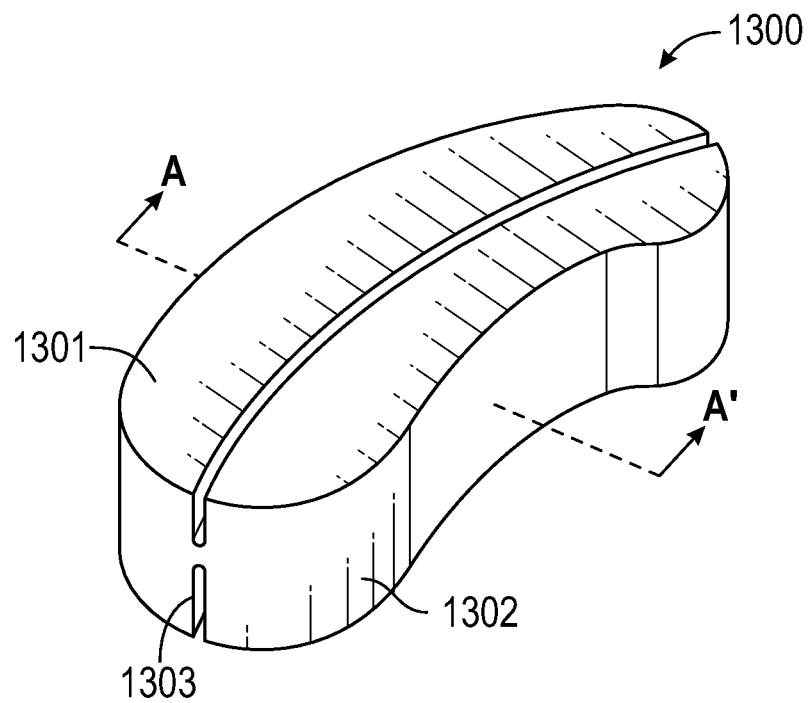
FIG. 13 illustrates an asymmetrical abduction cushion for a shoulder immobilizing apparatus, in accordance with some example embodiments.
Figures 14A, 14B:
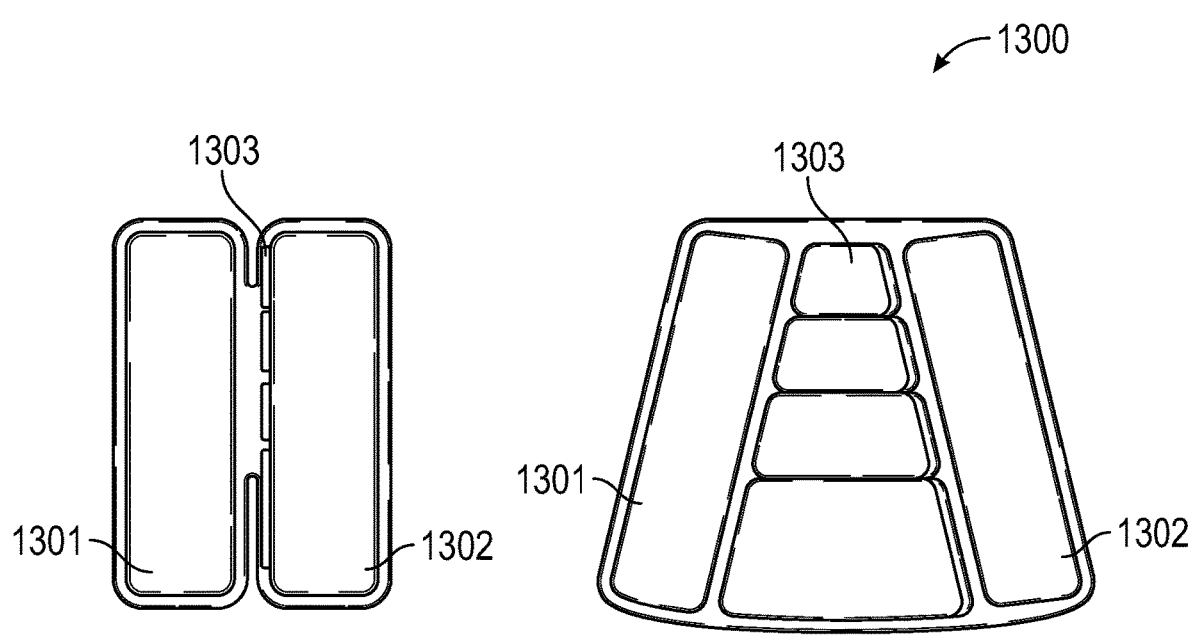
FIG. 14A illustrates a cross-sectional view of abduction cushion of FIG. 13 along cutline A-A' in an uninflated state, in accordance with some example embodiments.
FIG. 14B illustrates a cross-sectional view of abduction cushion of FIG. 13 along cutline A-A' in an inflated state, in accordance with some example embodiments.

FIG. 13 illustrates an asymmetrical abduction cushion 1300 for a shoulder immobilizing apparatus, in accordance with some example embodiments, while FIG. 14A illustrates a cross-sectional view of abduction cushion 1300 of FIG. 13 viewed along the cutline A-A' in an uninflated state, and FIG. 14B illustrates a cross-sectional view of abduction cushion 1300 of FIG. 13 viewed along the cutline A-A' in an inflated state. As illustrated in FIGS. 13-14B, asymmetrical abduction cushion 1300 may be configured to be disposed between forearm sling 110, 210, 310, 410, 510, 610, 710 and a torso of the user, thereby abducting the first arm of the user by a desired abduction angle. Abduction cushion 1300 includes a first padded cushion 1301, a second padded cushion 1302, and an inflatable bladder 1303 that, when inflated, is configured to separate a bottom portion of the first padded cushion 1301 from a bottom portion of the second padded cushion 1302 by a greater degree than a top portion of the first padded cushion 1301 from a top portion of the second padded cushion 1302, thereby achieving the desired abduction angle between the first arm and the torso of the user. In some embodiments, inflatable bladder 1303 can comprise a plurality of separate or interconnected cavities or chambers, each configured to inflate to a different size and/or width to affect the above-described inflation and abduction behavior. In some embodiments, one or both of first and second padded cushions 1301, 1302 can have a curved, concave and/or convex shape to aid proper locating and securing of abduction cushion 1300 between the arm or forearm and torso of the user. In some embodiments, one or both of padded cushions 1301, 1302 can comprise similar or the same materials as abduction cushion 1200.

Figure 15:
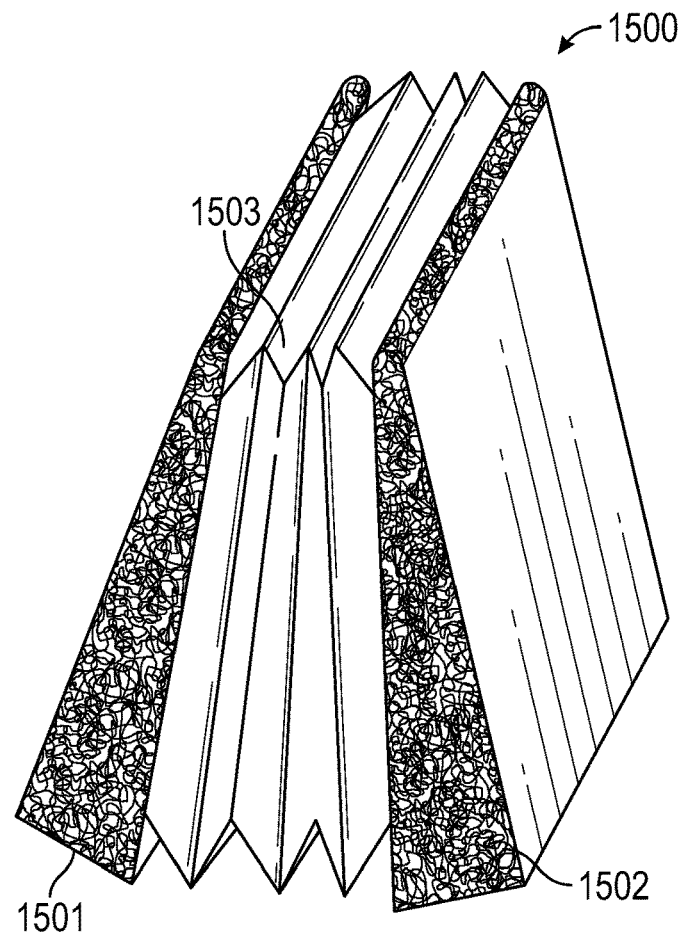
FIG. 15 illustrates another abduction cushion having an accordion-like bladder for a shoulder immobilizing apparatus, in accordance with some example embodiments.

FIG. 15 illustrates another abduction cushion 1500 having an accordion-like bladder 1503 for a shoulder immobilizing apparatus, in accordance with some example embodiments. As illustrated in FIG. 15, abduction cushion 1500 may be configured to be disposed between forearm sling 110, 210, 310, 410, 510, 610, 710 and a torso of the user, thereby abducting the first arm of the user by a desired abduction angle. Abduction cushion 1500 includes a first padded cushion 1501, a second padded cushion 1502, and an inflatable accordion-like bladder 1503 that, when inflated, is configured to separate first padded cushion 1501 from second padded cushion 1502. In some such embodiments, separation between first and second padded cushions 1501, 1502 can be unequal at the tops and bottoms of the padded cushions as described in connection with the cushion of FIGS. 13 and 14, thereby achieving the desired abduction angle between the first arm and the torso of the user. Alternatively, separation between first and second padded cushions 1501, 1502 can be equal at the tops and bottoms of the padded cushions, thereby achieving the desired abduction angle between the first arm and the torso of the user.

In some embodiments, one or both of first and second padded cushions 1501, 1502 can have a substantially wedge-shaped cross-section, for example as previously described in connection with FIG. 12. In some other embodiments, first and second padded cushions 1501, 1502 can have cross-sections with substantially uniform thickness.

In some embodiments, inflatable bladder 1503 can comprise an accordion-like cavity or chamber configured to inflate to affect the above-described inflation and abduction behavior. In some embodiments, one or both of first and second padded cushions 1501, 1502 can have any of a flat, curved, concave and/or convex shape to aid proper locating and securing of abduction cushion 1500 between the arm or forearm and torso of the user. In some embodiments, one or both of padded cushions 1501, 1502 can comprise similar or the same materials as abduction cushion 1200.

Figures 16A, 16B:
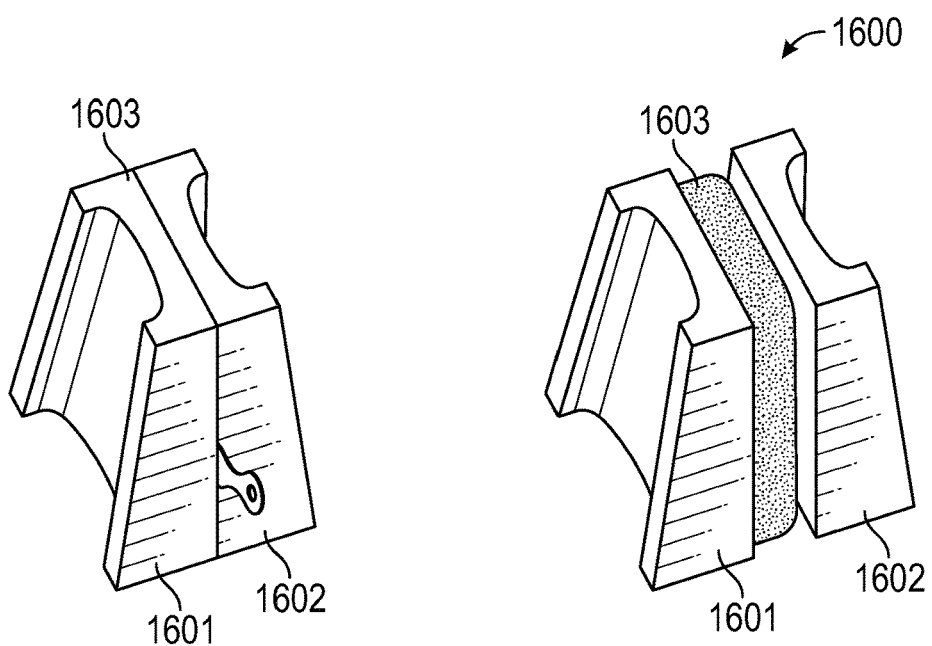
FIG. 16A illustrates yet another abduction cushion having an expandable vacuum bladder in an uninflated state for a shoulder immobilizing apparatus, in accordance with some example embodiments.
FIG. 16B illustrates the expandable vacuum bladder of FIG. 16A in an inflated state, in accordance with some example embodiments.

FIGS. 16A and 16B illustrate yet another abduction cushion 1600 having an expandable vacuum bladder 1603, in respective uninflated and inflated states, in accordance with some example embodiments. Abduction cushion 1600 may be configured to be disposed between forearm sling 110, 210, 310, 410, 510, 610, 710 and a torso of the user, thereby abducting the first arm of the user by a desired abduction angle. Abduction cushion 1600 includes a first padded cushion 1601, a second padded cushion 1602, and a vacuum bladder 1603 that, when having a vacuum pressure (i.e., a pressure less than ambient atmospheric pressure), is configured to bring first padded cushion 1601 and second padded cushion 1602 closer together (see, e.g., FIG. 16A) and, when having a smaller vacuum pressure (i.e., a pressure greater than that of the vacuum pressure described above), is configured to push first padded cushion 1601 and second padded cushion 1602 apart by virtue of an intrinsic expanding force of the material forming vacuum bladder 1603 that is not overcome by presence of a sufficient vacuum within vacuum bladder 1603 (see, e.g., FIG. 16B). In some such embodiments, separation between first and second padded cushions 1601, 1602 can be unequal at the tops and bottoms of the padded cushions as decribed in connection with the cushion of FIGS. 13-14B, thereby achieving the desired abduction angle between the first arm and the torso of the user. Alternatively, separation between first and second padded cushions 1601, 1602 can be equal at the tops and bottoms of the padded cushions, thereby achieving the desired abduction angle between the first arm and the torso of the user.

In some embodiments, one or both of first and second padded cushions 1601, 1602 can have a substantially wedge-shaped cross-section, with or without concave portions, for example as previously described in connection with FIG. 12. In some other embodiments, first and second padded cushions 1601, 1602 can have cross-sections with substantially uniform thickness. In some embodiments, one or both of first and second padded cushions 1601, 1602 can have any of a flat, curved, concave and/or convex shape to aid proper locating and securing of abduction cushion 1600 between the arm or forearm and torso of the user. In some embodiments, one or both of padded cushions 1601, 1602 can comprise similar or the same materials as abduction cushion 1200.

Figure 17A:
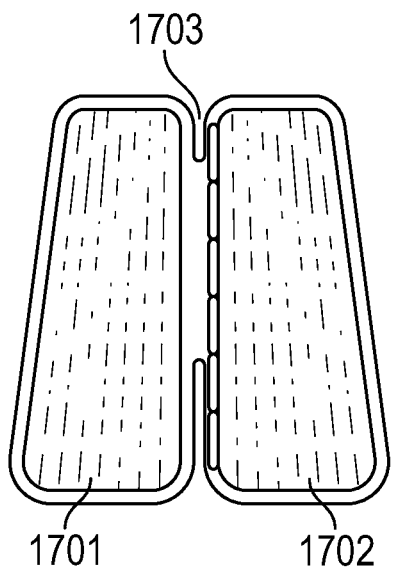
FIG. 17A illustrates a cross-sectional view of yet another abduction cushion having an expandable section in an uninflated state for a shoulder immobilizing apparatus, in accordance with some example embodiments.
Figure 17B:
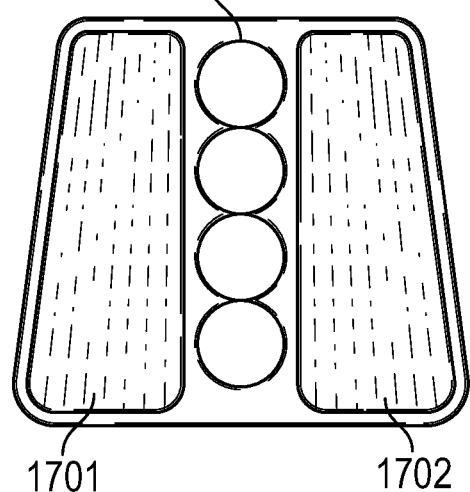
FIG. 17B illustrates a cross-sectional view of the expandable vacuum bladder of FIG. 17A in an inflated state, in accordance with some example embodiments.

FIGS. 17A and 17B illustrate yet another abduction cushion 1700 having an expandable section, in respective uninflated and inflated states, in accordance with some example embodiments. Abduction cushion 1700 may be configured to be disposed between forearm sling 110, 210, 310, 410, 510, 610, 710 and a torso of the user, thereby abducting the first arm of the user by a desired abduction angle. Abduction cushion 1700 includes a first padded cushion 1701, a second padded cushion 1702, and an inflatable bladder 1703 that, when inflated (see, e.g., FIG. 17B), is configured to separate first padded cushion 1701 from second padded cushion 1702. In some such embodiments, separation between first and second padded cushions 1701, 1702 can be unequal at the tops and bottoms of the padded cushions as decribed in connection with the cushion of FIGS. 13-14B, thereby achieving the desired abduction angle between the first arm and the torso of the user. Alternatively, separation between first and second padded cushions 1701, 1702 can be equal at the tops and bottoms of the padded cushions, thereby achieving the desired abduction angle between the first arm and the torso of the user.

In some embodiments, inflatable bladder 1703 can comprise a plurality of separate or interconnected, substantially circular cavities or chambers, each configured to inflate to a same or different size and/or width to affect the above-described inflation and abduction behavior. In some embodiments, one or both of first and second padded cushions 1701, 1702 can have a curved, concave and/or convex shape to aid proper locating and securing of abduction cushion 1700 between the arm or forearm and torso of the user. In some embodiments, one or both of padded cushions 1701, 1702 can comprise similar or the same materials as abduction cushion 1200.

In some embodiments, the user may desire to establish an abduction angle between the arm and torso of about 15 degrees. However, the present disclosure is not so limited and the user may desire to establish any suitable abduction angle. In some embodiments, an abduction angle of between 60-90 degrees is desirable, depending on the issue with the user's shoulder that requires immobilization.

Figure 18:
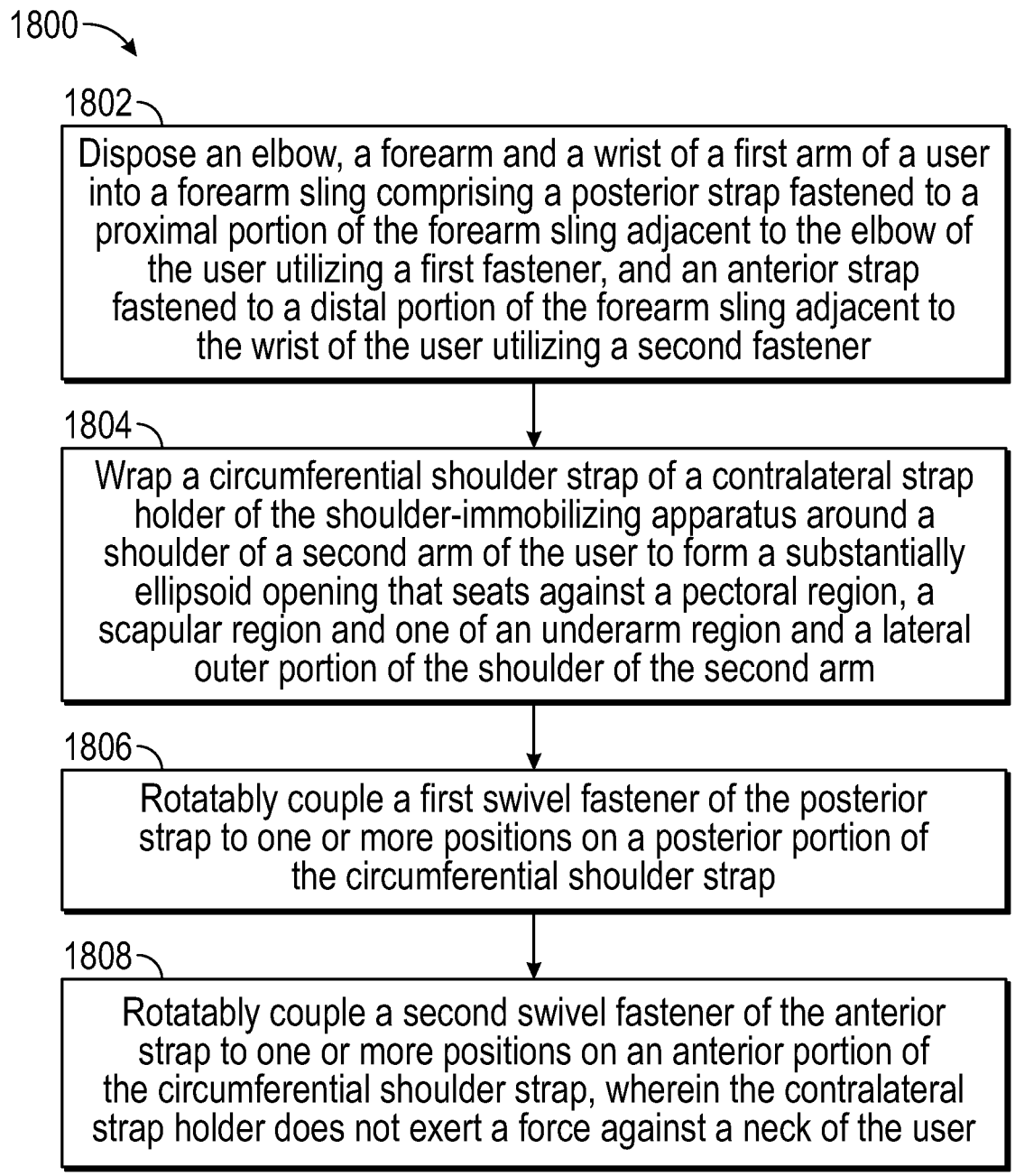
FIG. 18 illustrates a flowchart for a method of using a shoulder-immobilizing apparatus, in accordance with some example embodiments.

FIG. 18 illustrates a flowchart 1800 for a method of using any shoulder-immobilizing apparatus as described in this disclosure. Unless specifically stated, order of actions described by flowchart 1800 can be rearranged in any suitable order, one or more additional actions can be included, and/or one or more described actions can be omitted from such a method.

Block 1802 includes disposing an elbow, a forearm and a wrist of a first arm of a user into a forearm sling. For example, as previously described, a clinician or patient can dispose an elbow, a forearm and a wrist of a first arm of a user into any forearm sling 110, 210, 310, 410, 510, 610, 710 as previously described anywhere in this disclosure. Such a forearm sling can include a posterior strap 139 fastened to a proximal portion of the forearm sling 110 adjacent to the elbow of the user utilizing a first fastener 115 and an anterior strap 131 fastened to a distal portion of the forearm sling 110 adjacent to the wrist of the user utilizing a second fastener 114.

Block 1804 includes wrapping a circumferential shoulder strap of a contralateral strap holder of the shoulder-immobilizing apparatus around a shoulder of a second arm of the user to form a substantially ellipsoid opening that seats against a pectoral region, a scapular region and one of an underarm region and a lateral outer portion of the shoulder of the second arm. For example, as previously described, a clinician or patient can wrap a circumferential shoulder strap 138 of a contralateral strap holder 130 of the shoulder-immobilizing apparatus 100 around a shoulder of a second arm of the user to form a substantially ellipsoid opening 132 that seats against a pectoral region, a scapular region and one of an underarm region (see, e.g., FIGS. 1-2B, 11A and 11B) and a lateral outer portion of the shoulder (see, e.g., FIG. 10) of the second arm.

Block 1806 includes rotatably coupling a first swivel fastener of the posterior strap to one or more positions on a posterior portion of the circumferential shoulder strap. For example, as previously described, a clinician or patient can rotatably couple a first swivel fastener (see, e.g., fastener 133 for anterior strap 131) of the posterior strap 139 to one or more positions on a posterior portion of the circumferential shoulder strap 138.

Block 1808 includes rotatably coupling a second swivel fastener of the anterior strap to one or more positions on an anterior portion of the circumferential shoulder strap. For example, as previously described, a clinician or patient can rotatably couple a second swivel fastener 133 of the anterior strap 131 to one or more positions on an anterior portion of the circumferential shoulder strap 138.

In some embodiments, flowchart 1800 can further include adjusting a size of the substantially ellipsoid opening 132 of the circumferential shoulder strap 138 by overlapping opposite ends of the circumferential shoulder strap 138 by a desired amount at a top of the shoulder of the second arm and fastening the opposite ends to one another. In some embodiments, flowchart 1800 can further include any action associated with using, donning, attaching, fastening or adjusting any portion of any shoulder immobilizing apparatus as described in this disclosure.

Reference throughout this disclosure to "an embodiment" or "the embodiment" means that a particular feature, structure or characteristic described in connection with that embodiment is included in at least one embodiment. Thus, the quoted phrases, or variations thereof, as recited throughout this disclosure are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims. wherein the contralateral strap holder does not exert a force against a neck of the user Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Moreover, the present disclosure further contemplates methods of use and/or manufacture of any forearm sling described by this disclosure, which can include but are not limited to providing, installing, attaching, fitting, fabricating and/or configuring any portion of any forearm sling or accessory therefore as described anywhere in this disclosure. Various modifications, changes, and variations which will be apparent to those skilled in the art may be made in the arrangement, operation, and details of the methods and systems of the present disclosure disclosed herein without departing from the spirit and scope of the disclosure.

What is claimed is:

1. A shoulder-immobilizing apparatus, the apparatus comprising:
   a forearm sling configured to receive an elbow, a forearm and a wrist of a first arm of a user, the forearm sling further comprising:
      a first fastener configured for fastening a posterior strap to a proximal portion of the forearm sling adjacent to the elbow of the user,
      a second fastener configured for fastening an anterior strap to a distal portion of the forearm sling adjacent to the wrist of the user;
   a contralateral strap holder comprising:
      a circumferential shoulder strap configured to wrap around a shoulder of a second arm of the user to form an ellipsoid opening that seats against a pectoral region, a scapular region and a lateral outer portion of the second arm,
      the posterior strap having a first swivel fastener configured to rotatably couple to one or more positions on a posterior portion of the circumferential shoulder strap, and
      the anterior strap having a second swivel fastener configured to rotatably couple to one or more positions on an anterior portion of the circumferential shoulder strap,
      wherein the contralateral strap holder does not exert a force against a neck of the user; and
   an abduction cushion configured to be disposed between the forearm sling and a torso of the user, thereby abducting the first arm of the user by a desired abduction angle, the abduction cushion comprising:
      a first padded cushion;
      a second padded cushion; and
      a vacuum bladder disposed between the first and second padded cushions, the vacuum bladder formed of a material configured to exert an intrinsic expanding force such that:
         applying a vacuum pressure sufficiently below ambient atmospheric pressure to the vacuum bladder overcomes the intrinsic expanding force of the material of the vacuum bladder, thereby contracting the vacuum bladder and bringing the first and second padded cushions closer together, and
         the vacuum bladder is held in an at least partially expanded state by the expanded intrinsic expanding force of the material of the vacuum bladder when a pressure greater than the vacuum pressure is applied to the vacuum bladder.

2. The shoulder-immobilizing apparatus of claim 1, wherein the forearm sling further comprises a plurality of breathable holes.

3. The shoulder-immobilizing apparatus of claim 2, wherein each of the plurality of breathable holes have one or more of a circular shape, an ovoid shape, a rectangular shape and a rectangular shape with rounded corners.

4. The shoulder-immobilizing apparatus of claim 2, wherein the plurality of breathable holes have a maximum diameter of 1/16th of an inch or less, thereby being configured to prevent window edema in the first arm of the user.

5. The shoulder-immobilizing apparatus of claim 1, wherein the circumferential shoulder strap further comprises:
at least a first grommet configured to receive a first swivel post of the first swivel fastener of the posterior strap, thereby allowing the posterior strap to extend, unwrinkled and unfolded, between the forearm sling and the circumferential shoulder strap; and
at least a second grommet configured to receive a second swivel post of the second swivel fastener of the anterior strap, thereby allowing the anterior strap to extend, unwrinkled and unfolded, between the forearm sling and the circumferential shoulder strap.

6. The shoulder-immobilizing apparatus of claim 5, wherein:
the first grommet is one of a first plurality of grommets each designated with a different color, number or letter on the circumferential shoulder strap; and
the second grommet is one of a second plurality of grommets each designated with a different color, number or letter on the circumferential shoulder strap.

7. The shoulder-immobilizing apparatus of claim 1, wherein the ellipsoid opening of the circumferential shoulder strap is symmetrical about a centerline of the ellipsoid opening such that forearm sling is configured for use with either arm of the user without substantial adjustment.

8. The shoulder-immobilizing apparatus of claim 1, wherein the circumferential shoulder strap comprises opposite ends having one or more fasteners, the opposite ends configured to overlap one another at a top of the ellipsoid opening and rest against a top of the shoulder of the second arm.

9. The shoulder-immobilizing apparatus of claim 1, wherein the forearm sling further comprises a cutout configured to expose the elbow of the first arm of the user such that the forearm sling does not physically contact the elbow when the first arm is disposed in the forearm sling.

10. The shoulder-immobilizing apparatus of claim 1, wherein the forearm sling further comprises at least one cutout configured to expose an upper portion of the forearm of the first arm of the user such that the forearm sling does not physically contact the upper portion of the forearm when the first arm is disposed in the forearm sling.

11. The shoulder-immobilizing apparatus of claim 1, wherein the abduction cushion comprises one of a curved, concave or convex shape to aid proper locating and securing of the abduction cushion.

12. The shoulder-immobilizing apparatus of claim 1, wherein the vacuum bladder
is configured to separate a bottom portion of the first padded cushion from a bottom portion of the second padded cushion by a greater degree than a top portion of the first padded cushion from a top portion of the second padded cushion, thereby achieving the desired abduction angle between the first arm and the torso of the user.

13. The shoulder-immobilizing apparatus of claim 1, wherein the first padded cushion and the second padded cushion each have a uniform thickness.

14. A method of using a shoulder-immobilizing apparatus, the method comprising:
disposing an elbow, a forearm and a wrist of a first arm of a user into a forearm sling comprising:
a posterior strap fastened to a proximal portion of the forearm sling adjacent to the elbow of the user utilizing a first fastener, and
an anterior strap fastened to a distal portion of the forearm sling adjacent to the wrist of the user utilizing a second fastener;
wrapping a circumferential shoulder strap of a contralateral strap holder of the shoulder-immobilizing apparatus around a shoulder of a second arm of the user to form an ellipsoid opening that seats against a pectoral region, a scapular region and a lateral outer portion of the second arm;
rotatably coupling a first swivel fastener of the posterior strap to one or more positions on a posterior portion of the circumferential shoulder strap;
rotatably coupling a second swivel fastener of the anterior strap to one or more positions on an anterior portion of the circumferential shoulder strap; and
disposing an abduction cushion between the forearm sling and a torso of the user, thereby abducting the first arm of the user by a desired abduction angle,
wherein the abduction cushion comprises:
a first padded cushion;
a second padded cushion; and
a vacuum bladder disposed between the first and second padded cushions, the vacuum bladder formed of a material configured to exert an intrinsic expanding force such that:
applying a vacuum pressure sufficiently below ambient atmospheric pressure to the vacuum bladder overcomes the intrinsic expanding force of the material of the vacuum bladder, thereby contracting the vacuum bladder and bringing the first and second padded cushions closer together, and
the vacuum bladder is held in an at least partially expanded state by the intrinsic expanding force of the material of the vacuum bladder when a pressure greater than the vacuum pressure is applied to the vacuum bladder; and
wherein the contralateral strap holder does not exert a force against a neck of the user.

15. The method of claim 14, further comprising adjusting a size of the ellipsoid opening of the circumferential shoulder strap by overlapping opposite ends of the circumferential shoulder strap by a desired amount at a top of the shoulder of the second arm and fastening the opposite ends to one another.

* * * * *